United States Patent
Guillon et al.

(10) Patent No.: US 8,618,342 B2
(45) Date of Patent: Dec. 31, 2013

(54) PROCESS FOR THE PRODUCTION OF ALKYLBENZENES FROM AN OLEFINIC FEEDSTOCK PRODUCED BY OLIGOMERIZATION THAT IS CATALYZED HOMOGENEOUSLY

(75) Inventors: Emmanuelle Guillon, Vourles (FR); Eric Sanchez, Saint Genis Laval (FR)

(73) Assignee: IFP Energies nouvelles, Rueil-Malmaison Cedex (FR)

( * ) Notice: Subject to any disclaimer, the term of this patent is extended or adjusted under 35 U.S.C. 154(b) by 174 days.

(21) Appl. No.: 13/101,204

(22) Filed: May 5, 2011

(65) Prior Publication Data
US 2011/0282121 A1 Nov. 17, 2011

(30) Foreign Application Priority Data
May 6, 2010 (FR) ...................................... 10 01949

(51) Int. Cl.
C07C 2/32 (2006.01)
C07C 2/34 (2006.01)

(52) U.S. Cl.
USPC ........... 585/323; 585/455; 585/510; 585/517; 585/521

(58) Field of Classification Search
USPC .......................... 585/323, 455, 510, 517, 521
See application file for complete search history.

(56) References Cited

U.S. PATENT DOCUMENTS

| | | | |
|---|---|---|---|
| 4,891,457 A | 1/1990 | Owen et al. | |
| 4,959,491 A | 9/1990 | Threlkel | |
| 5,345,023 A | 9/1994 | Chauvin et al. | |
| 6,444,866 B1 | 9/2002 | Commereuc et al. | |

FOREIGN PATENT DOCUMENTS

| | | |
|---|---|---|
| EP | 0 215 609 A1 | 3/1987 |
| EP | 0 578 541 A1 | 1/1994 |
| FR | 2 765 573 A1 | 1/1999 |
| WO | WO 88/07030 A2 | 9/1988 |

OTHER PUBLICATIONS

Search Report of FR 1001949 (Oct. 21, 2010).

*Primary Examiner* — Thuan D Dang
(74) *Attorney, Agent, or Firm* — Millen, White, Zelano & Branigan, P.C.

(57) ABSTRACT

A process for the production of a mixture of alkylbenzenes in the presence of an aromatic feedstock and an olefinic stream produced from an ethylene feedstock is described, with said process comprising at least:
a) A first stage for oligomerization of said ethylene feedstock that consists of at least one hydrocarbon effluent that comprises a mixture of olefins having a number of carbon atoms that is for the most part between 4 and 30, whereby said mixture of olefins comprises a C10-C24 olefinic fraction that has a mean linearity that is greater than 60%, in the presence of a homogeneous catalytic system,
b) A second stage for oligomerization of the effluent that is obtained from said stage a) that consists of at least one hydrocarbon effluent that comprises a mixture of olefins having a number of carbon atoms that is for the most part between 4 and 30, whereby said mixture of olefins comprises a C10-C24 olefinic fraction that has a mean linearity that is less than 50%, in the presence of a homogeneous catalytic system that is identical to or different from the one that is used in said stage a),
c) A stage for fractionation of the effluent that is obtained from said oligomerization stage b) in such a way as to recover at least one olefin-enriched olefinic stream having a number of carbon atoms that is greater than or equal to 9,
d) A stage for alkylation of said olefinic stream by an aromatic feedstock.

14 Claims, 1 Drawing Sheet

PROCESS FOR THE PRODUCTION OF ALKYLBENZENES FROM AN OLEFINIC FEEDSTOCK PRODUCED BY OLIGOMERIZATION THAT IS CATALYZED HOMOGENEOUSLY

TECHNICAL FIELD

This invention relates to the field of the production of aromatic compounds that belong to the families of alkylbenzenes by a non-conventional method that uses a feedstock that is produced by oligomerization catalyzed homogeneously as an olefinic feedstock for the implementation of an alkylation stage. The alkylbenzenes that are obtained according to the process of the invention constitute precursors of choice for the formulation of detergents and in particular biodegradable detergents, for example by sulfonation.

PRIOR ART

The alkylbenzenes are generally produced by alkylation of aromatic compounds, preferably by alkylation of benzene, by means of olefin(s) having 9 to 16, preferably 10 to 14, carbon atoms per molecule. The conventional processes of the production of alkylbenzenes use olefins that are obtained from petroleum fractions that have undergone several treatments before being able to be used as an olefinic reagent for the alkylation reaction in the presence of benzene. In particular, the conventional processes for the production of alkylbenzenes most often comprise the concatenation of the following stages:

1—The separation of normal paraffins that are present in a C9-C16 fraction,
2—The dehydrogenation of normal paraffins into C9-C16 olefins,
3—The selective hydrogenation of the diolefins that are produced during said dehydrogenation stage 2),
4—The optional elimination of the aromatic compounds that are produced during said stage 2) by any means that is known to one skilled in the art (separation, adsorption, . . . ),
5—The alkylation of benzene by the C9-C16 olefins so as to produce alkylbenzenes in the presence of an acid catalyst in solid form (silica-alumina, zeolites, clays) or in liquid form (HF).

Such a process for the production of alkylbenzenes has already been widely described, for example in the U.S. Pat. No. 5,245,094, U.S. Pat. No. 5,276,231 and U.S. Pat. No. 5,334,793 as well as in Ullmann's Encyclopedia, 5$^{th}$ Volume A 25, page 766.

So as to limit the formation of undesirable compounds, in particular those of aromatic compounds, said conventional processes for the production of alkylbenzenes, starting from a paraffinic fraction as an olefin source for the alkylation reaction, operate under conditions such that the conversion of the paraffins into olefins remains low; the conversion of normal paraffins into olefins, per pass, is generally estimated to be between 5 and 30% over the dehydrogenation stage (stage 2 indicated above). This low conversion constitutes a major drawback of this type of process to the extent that the desired olefins are produced in a small quantity and that the normal paraffins, not converted into said dehydrogenation stage, are present, in a large proportion, in the feedstocks that are introduced into the reactors that implement the stages for selective hydrogenation (stage 3 above), elimination of aromatic compounds (stage 4 above), and alkylation (stage 5 above). The low conversion of normal paraffins into olefins therefore constitutes a major drawback since said stages 3, 4, and 5 undergo the presence of such paraffins without being able to be transformed, creating a significant dimensioning of the process and inevitably bringing about major consequences in terms of investment and operating costs. In addition, the presence of a large quantity of paraffins in the reactor that produces the alkylation stage is detrimental to the alkylation catalyst that then deactivates quickly.

Furthermore, the advantage of producing modified alkylbenzenes (MAB), whose alkyl chain is branched (WO 99/05082, U.S. Pat. No. 6,525,233) for the purpose of an improvement in the solubility of linear alkylbenzene sulfonates (LAS for linear alkylbenzene sulfonates) at low temperature, an improvement in their sensitivity to the hardness of water, and an improvement in their detergent properties, was taught. However, the conventional processes for the production of alkylbenzenes lead to the production of linear alkylbenzenes (LAB) whose alkyl chain is lacking in any branching. Also, to meet the demand for modified alkylbenzenes, processes were considered that integrate an additional stage for isomerization of the paraffins placed either upstream from the process (WO 01/05733, U.S. Pat. No. 6,187,981) or between the selective hydrogenation stage and the alkylation stage (U.S. Pat. No. 6,670,516). The introduction of an isomerization stage adds to the complexity of the concatenation of the processes for the production of alkylbenzenes, which then comprise at least 6 stages.

In such a way as to remedy the drawbacks encountered by the implementation of the conventional processes for the production of alkylbenzenes, this invention proposes providing a new process for the production of alkylbenzenes of which one of the intermediate stages, prior to the implementation of the alkylation stage, leads to the production of an effluent that is composed for the most part of branched olefins, thus avoiding not only the implementation of an isomerization stage but also the undesirable presence of paraffins in the alkylation reactor; this accounts for an improved stability of the alkylation catalyst, in particular when the latter is an acidic solid catalyst, for example a zeolitic catalyst. The process according to the invention uses an ethylene feedstock as an olefin source and does not produce intermediate effluents that contain undesirable compounds, such as paraffins or aromatic compounds in the prior processes, for the concatenation of the different stages: the dimensioning of the process according to the invention is thus better adjusted to the strict requirement for production of alkylbenzenes without the necessity of using large capacities, in particular at the level of the dimensioning of different reactors, for incorporating unconverted and/or undesirable compounds. The process according to the invention, while avoiding the necessity for initiating recycling of paraffinic streams and the elimination of aromatic compounds, makes it possible to produce, with investment and operating costs that are considerably reduced relative to those of the prior art, a quality of desired alkylbenzenes for then being updated in the formulation of biodegradable detergents.

DESCRIPTION OF THE INVENTION

This invention has as its object a process for the production of a mixture of aromatic compounds belonging to the family of alkylbenzenes in the presence of at least one aromatic feedstock that comprises at least one compound that has a benzene core and at least one olefinic stream that is produced from an ethylene feedstock, whereby said process comprises at least:

a) A first stage for oligomerization of said ethylene feedstock that consists of at least one hydrocarbon effluent that comprises a mixture of olefins having a number of carbon atoms that is for the most part between 4 and 30, whereby said mixture of olefins comprises a C10-C24 olefinic fraction that has a mean linearity that is greater than 60%, in the presence of at least one homogeneous catalytic system that contains at least one metal precursor that comprises at least one transition metal that is selected from among titanium, zirconium, hafnium, nickel, and iron, taken by themselves or in a mixture, b) A second stage for oligomerization of the effluent that is obtained from said stage a) that consists of at least one hydrocarbon effluent that comprises a mixture of olefins having a number of carbon atoms that is for the most part between 4 and 30, whereby said mixture of olefins comprises a C10-C24 olefinic fraction that has a mean linearity that is less than 50%, in the presence of at least one homogeneous catalytic system that is identical to or different from the one that is used in said stage a), c) At least one stage for fractionation of the effluent that is obtained from said oligomerization stage b) in such a way as to recover at least one olefin-enriched olefinic stream having a number of carbon atoms that is greater than or equal to 9, d) A stage for alkylation of said olefinic stream that is obtained from said stage c) by at least one aromatic feedstock that comprises at least one compound that has a benzene core.

In accordance with said stage a), said ethylene feedstock that is used for the implementation of said stage a) for the most part comprises ethylene, i.e., at least 60% by weight, and preferably at least 75% by weight of ethylene. In a very preferred manner, said ethylene feedstock consists entirely of ethylene. It can come from varied sources; for example, it can come from fossil resources or non-fossil resources. In particular, said ethylene feedstock advantageously comes from a steam-cracking unit, an FCC unit, or a Fischer-Tropsch synthesis unit.

The term FCC refers to the process for catalytic cracking in a fluidized bed of petroleum fractions with a boiling point that is higher than approximately 350° C., for example a vacuum distillate, optionally deasphalted oil, or an atmospheric residue. The C2 fraction of the FCC effluent that can advantageously be used as an ethylene feedstock for the implementation of said stage a) of the process according to the invention comprises ethylene and ethane as well as other compounds that comprise 2 carbon atoms, such as acetylene. Said C2 fraction that is obtained from an FCC unit is preferably pretreated before being used for the implementation of said stage a) of the process according to the invention.

The naphtha steam-cracking (paraffinic hydrocarbon fraction that has at least the volatility of a gasoline) is a process that consists in producing olefins by thermal cracking of paraffinic hydrocarbons in the presence of water. The steam cracking produces the large intermediate products of petrochemistry: ethylene, propylene, butenes, butadiene and benzene.

The Fischer-Tropsch synthesis generally leads to the production of olefins, in particular ethylene, starting from synthetic gas that comes from, for example, fossil resources (carbon, gas, . . . ) or the gasification of renewable resources. For example, the Fischer-Tropsch processes that are catalyzed by the high-temperature iron systems are known for leading to the production of light fractions that are rich in olefins and in particular in ethylene. The synthetic gas can also be converted into methanol or ethanol, whereby ethanol can generate ethylene by dehydration.

So as to be free of the consumption of petroleum and to reduce the consumption of energy, said ethylene feedstock, used for the implementation of said stage a) of the process according to the invention, can also advantageously come from non-fossil resources, i.e., renewable sources such as those obtained from the cultivation of vegetables. In particular, said ethylene feedstock advantageously comes from the reaction of dehydration of bioethanol, which is produced from a renewable source that is obtained from the biomass. The bioethanol is produced biologically, more specifically by fermentation of sugars obtained from, for example, crops such as sugarcane (saccharose, glucose, fructose, sucrose), starch (glucose), beet scraps, or else obtained from amylased plants or lignocellulosic biomass or hydrolyzed cellulose (glucose for the most part, and xylose, galactose), containing variable quantities of water. The bioethanol is advantageously produced by fermentation from three sources: 1) sucrose from cane sugar or beet scraps, 2) starch that is present in grains and tubers, and 3) cellulose and hemicellulose that are present in wood, herbs and other lignocellulosic biomasses.

First of all, the vegetable material that is implemented in the production of bioethanol is advantageously pretreated and hydrolzyed according to the processes for pretreatment and hydrolysis of the biomass that are well known to one skilled in the art. The fermentation stages of the vegetable material in ethanol are also well known. They can advantageously implement one or more yeasts and are advantageously followed by a distillation that makes it possible to recover ethanol in aqueous form.

The reaction for dehydration of bioethanol, produced from a renewable source that is obtained from biomass, is advantageously implemented according to the teaching that is described in the publication "Ethylene from Ethanol" (N. K. Kochar, R. Merims, and A. S. Padia, CEP, June 1981) and in the U.S. Pat. No. 4,232,179, U.S. Pat. No. 4,396,789, U.S. Pat. No. 4,234,752, U.S. Pat. No. 4,396,789 and U.S. Pat. No. 4,698,452. Said dehydration reaction is preferably implemented in the presence of an acid catalyst that can be either amorphous or zeolitic.

The ethylene fraction that is obtained by dehydration of bioethanol is preferably subjected to at least one purification stage before being used in the first reaction zone for oligomerization for the implementation of said stage a) of the process according to the invention in such a way as to eliminate the impurities, in particular anionic impurities (ions of $Cl^-$, sulfate, nitrite, nitrate, phosphates) and cationic impurities (ions of $Na^+$, $Ca^{2+}$, $Mn^{2+}$, $Fe^{2+}$, $Cu^{2+}$, $Zn^{2+}$), and at least some, preferably all, of the oxidized compounds other than the alcohols (for example, ethers, acids, ketones, aldehydes and/or esters), present in said ethylene fraction, and to limit the deactivation of the homogeneous catalytic systems for oligomerization that are placed downstream. The purification stage is advantageously implemented by means that are known to one skilled in the art, such as, for example, the use of at least one resin, columns for washing with water and/or columns for washing with soda, the adsorption of impurities on solid selected from among the molecular sieves, active carbon, alumina and zeolites, distillation, the hydrogenation of organic compounds in the presence of a nickel-based catalyst, the absorption by a solvent (ionic liquid, etc) so as to obtain a purified ethylene feedstock that corresponds to the level of impurities compatible with the homogeneous oligomerization catalytic systems that are placed downstream.

In a general manner, the oligomerization refers to the addition of n olefins that are identical and/or different. The oligomerization is distinguished from the polymerization by an addition of molecules in a limited number. According to the invention, the number n is, for the largest part by weight of the oligomers, between 2 and 60, and preferably between 2 and 40.

In accordance with stage a) of the process according to the invention, said ethylene feedstock is subjected to a first oligomerization stage in such a way as to produce at least one hydrocarbon effluent that comprises a mixture of olefins having a number of carbon atoms that is for the most part between 4 and 30, whereby said mixture of olefins comprises a C10-C24 olefinic fraction, which has a mean linearity that is greater than 60% and preferably greater than 65%.

According to the invention, said hydrocarbon effluent that is obtained at the end of said first oligomerization stage comprises at least 50% by weight, preferably at least 70% by weight, of a mixture of olefins having a number of carbon atoms that is for the most part between 4 and 30, whereby the percentages are expressed in percentage by weight relative to the total mass of the hydrocarbon compounds that are present in said hydrocarbon effluent that is obtained at the end of stage a).

Throughout the rest of the description, a mixture of olefins is defined as having a number of carbon atoms that is for the most part between 4 and 30, whereby a mixture of olefins comprises at least 50% by weight, preferably at least 60% by weight, and in a more preferred manner at least 70% by weight of olefins having a number of carbon atoms of between 4 and 30, whereby the percentages are expressed in percentage by weight relative to the total mass of the mixture of olefins having a number of carbon atoms that is for the most part between 4 and 30.

In accordance with stage a) of the process according to the invention, said mixture of olefins having a number of carbon atoms that is for the most part between 4 and 30 preferably comprises less than 40% by weight, and in a more preferred manner less than 35% by weight, of a mixture of olefins having a number of carbon atoms of between 10 and 24 (C10-C24 olefinic fraction), whereby the addition is ensured by olefins that have 4 to 9 carbon atoms and 25 to 30 carbon atoms, whereby the percentages are expressed in percentage by weight relative to the total mass of the olefins that are present in said mixture. It is recalled that a C10-C24 olefinic fraction is defined as a mixture of olefins having a number of carbon atoms of between 10 and 24. Said C10-C24 olefinic fraction has a mean linearity that is greater than 60% and preferably greater than 65%. The mean linearity, expressed in terms of percentage, refers to the ratio of the percentage of linear olefins that are present in the C10-C24 olefinic fraction to the total percentage of olefins that are present in the C10-C24 olefinic fraction. The linearity is determined by a gas phase chromatography analysis carried out on the C10-C24 olefinic fraction after said fraction is hydrogenated.

Said first stage a) for oligomerization of the ethylene feedstock is implemented by homogeneous catalysis, i.e., the catalyst that is used for the implementation of said stage is soluble in the oligomerization products for forming a single liquid phase. Said first oligomerization stage a) is carried out in the presence of at least one homogeneous catalytic system that contains at least one metal precursor that comprises at least one transition metal that is selected from among titanium, zirconium, hafnium, nickel, and iron, taken by themselves or in a mixture, preferably selected from among nickel, zirconium, and iron.

Preferably, the homogeneous catalytic system that is used in said first oligomerization stage a) contains in addition to at least one metal precursor that comprises at least one transition metal that is selected from among titanium, zirconium, hafnium, nickel and iron, taken by themselves or in a mixture—at least one activator that is preferably selected from the group that is formed by tris(hydrocarbyl)aluminum, hydrocarbylaluminum halides, preferably chlorinated or brominated hydrocarbylaluminum compounds, and aluminoxanes. The tris(hydrocarbyl)aluminum and the hydrocarbylaluminum halides preferably correspond to the general formula $AlR''_n Y_{3-n}$, in which R'' represents a monovalent hydrocarbon radical that contains, for example, up to 12 carbon atoms such as alkyl, aryl, aralkyl, alkaryl or cycloalkyl; Y represents a halogen atom that is preferably selected from among chlorine and bromine, and very preferably Y is chlorine, whereby n can assume a value of 0 to 3.

The tris(hydrocarbyl)aluminum and the hydrocarbylaluminum halides that correspond to the general formula $AlR''_n Y_{3-n}$ are preferably selected from among ethyl aluminum sesquichloride (EASC), dichloroethylaluminum (EADC), dichloroisobutylaluminum, chlorodiethylaluminum (DEAC), triethylaluminum (TEA) and trimethylaluminum (TMA). These activators can be used alone or in a mixture.

The aluminoxanes are preferably selected from among methylaluminoxane (MAO) or modified methylaluminoxane (MMAO), taken by themselves or in a mixture.

Said homogenous catalytic system that is used in said first oligomerization stage a) advantageously contains at least one additive that is selected from among the Bronsted acid compounds, the Lewis acids and bases, and the electron donor organic compounds that contain at least one oxygen atom or at least one nitrogen atom or at least one phosphorus atom or at least one monofunctional or polyfunctional sulfur atom. By way of example, it is possible to cite amines, imines, carboxylic acids, acetals, ketals, ethers or alcohols.

According to a first preferred embodiment of said first oligomerization stage a), said metal precursor that is present in the homogeneous catalytic system comprises nickel. Such a nickel-based homogenous catalytic system can be prepared by any method that is known to one skilled in the art, for example by one of the methods that are described in the patent application US 2008/033,224 or in the U.S. Pat. No. 7,235,703 and U.S. Pat. No. 4,362,650. Preferably, said homogenous catalytic system comprises at least one bivalent nickel compound, at least one hydrocarbylaluminum halide, preferably a chlorinated or brominated hydrocarbylaluminum compound that is selected from among ethyl aluminum sesquichloride (EASC), dichloroethylaluminum (EADC), dichloroisobutylaluminum and chlorodiethylaluminum (DEAC) as activator, and optionally at least one Bronsted acid compound or at least one electron donor organic compound as an additive.

In accordance with said first preferred embodiment, the nickel-based metal precursors that are selected from among the nickel carboxylates of general formula $(R_1COO)_2Ni$, where $R_1$ is a hydrocarbyl radical, for example, alkyl, cycloalkyl, alkenyl, aryl, aralkyl or alkaryl, containing up to 20 carbon atoms, are advantageously suitable for the implementation of said homogeneous catalytic system. The radical R1 is, for example, a hydrocarbyl radical that has 5 to 20 carbon atoms or else an alkylene radical that has 6 to 18 carbon atoms. The radical $R_1$ can be substituted by one or more halogen atoms, one or more hydroxy, ketone, nitro or cyano groups, or other groups that do not hamper the reaction. Nonlimiting examples of nickel precursors are the following bivalent nickel salts: octoate, ethyl-2 hexanoate, decanoate, stearate, oleate, salicylate, and hydroxydecanoate. The nickel bis(ethyl-2 hexanoate) is preferably used as a precursor of the nickel.

The Bronsted acid compound, advantageously present in the homogeneous catalytic system that is used for the implementation of said first preferred embodiment, corresponds to the formula HY, where Y is an organic anion, for example carboxylate, sulfonate or phenolate. The acid compounds of which the $pK_a$ at 20° C. is at most equal to 3, more particularly those that are soluble in the precursor of nickel or in its solution in a hydrocarbon or another suitable solvent, are preferred. A preferred class of Bronsted acid compounds comprises the group that is formed by the halocarboxylic acids of formula $R_2COOH$ in which $R_2$ is a halogenated alkyl radical, in particular those that contain at least one halogen atom of alpha of the group —COOH with a total of 2 to 10 carbon atoms. Preferably, a haloacetic acid of formula $CX_pH_{3-p}$—COOH, in which X is fluorine, chlorine, bromine or iodine, with p being an integer from 1 to 3, is used. By way of example, it is possible to cite the following acids: trifluoroacetic, difluoroacetic, fluoroacetic, trichloroacetic, dichloroacetic, and chloroacetic. These examples are not limiting, and it is also possible to use the following acids: arylsulfonic, alkylsulfonic, fluoroalkylsulfonic, and picric acid, and nitroacetic acid. Trifluoroacetic acid is preferably used.

According to a second preferred embodiment of said first oligomerization stage a), said metal precursor that is present in the homogeneous catalytic system comprises zirconium. Such a zirconium-based homogeneous catalytic system can be prepared by any method that is known to one skilled in the art, for example by one of the methods described in the patent application FR 2 693 455. Preferably, said homogeneous catalytic system contains at least one zirconium-based precursor, at least one compound of aluminum as an activator that is selected from among the compounds that are described above, and optionally at least one electron donor organic compound as an additive. The zirconium-based metal precursors are advantageously selected from among the zirconium halides, such as zirconium tetrachloride $ZrCl_4$ and zirconium tetrabromide $ZrBr_4$, the alcoholates such as zirconium tetrapropylate $Zr(OC_3H_7)_4$, and zirconium tetrabutylate $Zr(OC_4H_9)_4$, the carboxylates such as zirconium tetra-ethyl-2-hexanoate $Zr(OCOC_7H_{15})_4$ and the oxo-carboxylates such as dizirconium 1-oxo-hexaethyl-2-hexanaote $[Zr(OCOC_7H_{15})_3]_2O$.

The organic compounds, used as an additive in the homogeneous catalytic system that is advantageously used for the implementation of said preferred second embodiment, are advantageously selected from among the class of acetals and ketals. By way of example, it is possible to cite diethoxymethane, diisopropoxymethane, diethoxy-1,1-ethane, diisobutoxy-1,1-ethane, dimethoxy-1,1-decane, nonyl-2-dioxolane-1,3, dimethoxy-2,2-propane, dibutoxy-2,2-propane, dioctoxy-2,2-propane, di(2-ethylhexyloxy)-2,2-propane, dimethoxy-2,2-octane, and dimethoxy-1,1-cyclohexane.

According to a third preferred embodiment of said first oligomerization stage a), said metal precursor that is present in the homogeneous catalytic system comprises titanium. Such a titanium-based homogeneous catalytic system can be prepared by any method that is known to one skilled in the art, for example by one of the methods that is described in the U.S. Pat. No. 3,660,519, U.S. Pat. No. 3,879,485, FR 8315041, U.S. Pat. No. 3,584,071 or EP 0,722,922 B1. Preferably, said homogeneous catalytic system contains at least one titanium-based precursor, at least one compound of aluminum as an activator that is selected from among the compounds described above, and optionally at least one organic compound as an additive. The titanium-based metal precursors are advantageously selected from among the compounds that correspond to the general formula $X_nTi(OR)_{4-n}$ in which X is a chlorine or bromine atom, a hydrocarbyl radical that comprises 1 to 30 carbon atoms, or a radical that is selected from the group that is formed by the $R'_2N^-$ amidos and the $R'COO^-$ carboxylases, where R' is selected from among a hydrocarbyl radical that comprises 1 to 30 carbon atoms, and a cyclopentadienyl ligand that may or may not be substituted, whereby n is an integer of between 0 and 4. The radical —OR is an organic compound that is selected from the family of aryloxy or alkoxy ligands, optionally substituted by aryl or aralkyl groups or by heteroatoms.

The organic compounds that are used as an additive, in the homogeneous catalytic system that is advantageously used for the implementation of said third preferred embodiment, are advantageously selected from among the electron donor organic compounds that contain at least one oxygen atom or at least one nitrogen atom or at least one phosphorus atom or at least one sulfur atom. Without being limiting, it is possible to cite tetrahydrofuran or dibutyl ether.

According to a fourth preferred embodiment of said first oligomerization stage a), said metal precursor that is present in the homogeneous catalytic system comprises iron. Such an iron-based homogeneous catalytic system can be prepared by any method that is known to one skilled in the art, for example by one of the methods described in the patent applications WO99/02472, WO 02/06192 A1 or WO2005/080301A1 or else in the publications by V. Gibson, Chem. Rev. 2007, 107, 1745, or Britovek et al., Chem. Eur. J., 2000, 6, 12, pp. 2221-2231. Preferably, said homogeneous catalytic system contains at least one iron complex, at least one aluminum compound as an activator, and optionally at least one electron donor organic compound as an additive. The iron-based metal precursors are advantageously selected from among $FeCl_2$; $FeCl_2,4H_2O$; $FeCl_2$, 1.5THF; $FeCl_2$, 2-pyridine; $FeBr_2$; $Fe(NSiMe_3)_2$; $Fe(CH_3COO)_2$; $Fe(C_6H_5N)_2(CH_3SiMe_3)_2$; $Fe(NO_3)_2$; $Fe(CF_3SO_3)_2$; $Fe(ethyl-2-hexanoate)_2$, and the complexes of bis(imino)pyridine of Fe(II) or Fe(III).

The activating agent that is present in the homogeneous catalytic system, advantageously used for the implementation of said fourth preferred embodiment, is preferably selected from among the aluminum compounds and is preferably an aluminoxane that is selected from among methylaluminoxane (MAO) and modified methylaluminoxane (MMAO), taken by themselves or in a mixture.

In accordance with said first oligomerization stage a), a preferred homogeneous catalytic system, for the implementation of said first stage, contains at least one zirconium-based metal precursor and at least one activator that is based on ethyl aluminum sesquichloride.

The second oligomerization stage b) therefore has as its objective to promote the shift of the distribution of olefins to the C10-C24 fraction and to reduce its mean linearity.

In accordance with said stage b) of the process according to the invention, at least some, i.e., at least 50% by weight of the effluent that is obtained from said stage a), and preferably all of the effluent that is obtained from stage a), is sent into a second reaction zone that implements a second oligomerization stage b) for producing at least one hydrocarbon effluent that comprises a mixture of olefins having a number of carbon atoms that is for the most part between 4 and 30, whereby said mixture of olefins comprises a C10-C24 olefinic fraction that has a mean linearity that is less than 50%, in the presence of at least one homogeneous catalytic system, identical to or different from the one that is used in said stage a).

According to the invention, said hydrocarbon effluent that is obtained at the end of said second oligomerization stage b) comprises at least 50% by weight, preferably at least 70% by weight, of a mixture of olefins having a number of carbon atoms that is for the most part between 4 and 30, whereby the percentages are expressed in percentage by weight relative to the total mass of the hydrocarbon compounds that are present in said effluent that is obtained at the end of stage b).

In accordance with said stage b) of the process according to the invention, said mixture of olefins having a number of carbon atoms that is for the most part between 4 and 30 preferably comprises at least 45% by weight, and in a more preferred manner at least 50% by weight, of a mixture of olefins having a number of carbon atoms that is for the most part between 10 and 24 (C10-C24 olefinic fraction), whereby the percentages are expressed in terms of percentage by weight relative to the total mass of the olefins that are present in said mixture. Said C10-C24 fraction has a mean linearity that is less than 50% and preferably less than 40%.

According to a first preferred embodiment of said second oligomerization stage b), the homogeneous catalytic system that is used in the second oligomerization stage b) is identical to the one that is used in the first oligomerization stage a), i.e., the transition metal(s) that are present in said metal precursor(s) is (are) identical in each of said catalytic systems. Said catalytic system that is used in the second oligomerization stage b), identical to the one that is used in the first oligomerization stage a), advantageously contains at least one activator and/or at least one additive that has a composition that is selected from among the one that is described earlier in this description, whereby said activator and said additive have a composition that is identical to or different from the one that is optionally used for the implementation of said homogeneous catalytic system that is present in said first oligomerization stage a). According to a very preferred mode of said first preferred embodiment of said second oligomerization stage b), the homogeneous catalytic system contains a zirconium-based metal precursor, a first activator that is based on ethyl aluminum sesquichloride, and at least a second activator that is preferably based on triethylaluminum (TEA).

The addition of at least one activator in the second oligomerization stage b) makes it possible to increase significantly the proportion by weight of the C10-C24 olefinic fraction in the mixture of olefins that is present in the hydrocarbon effluent that is obtained at the end of said second oligomerization stage b).

According to a second preferred embodiment of said second oligomerization stage b), the homogeneous catalytic system that is used in the second oligomerization stage b) is different from the one that is used in the first oligomerization stage a). In this case and in a very preferred manner, said homogeneous catalytic system contains at least one metal precursor that comprises at least one transition metal that is selected from among titanium, zirconium, hafnium, nickel, and iron, taken by themselves or in a mixture. Said homogeneous catalytic system advantageously contains at least one activator and/or at least one additive. The activators and the additives that are used for the implementation of the homogeneous catalytic system that is used in the first oligomerization stage and described earlier in this description are suitable for the implementation of the homogeneous catalytic system that is used in the first oligomerization stage.

The preparation of homogeneous catalytic systems is well known to one skilled in the art. For example, the preparation of each of the homogeneous catalytic systems used for the implementation of said stages a) and b) comprises bringing, in any order whatsoever, at least one metal precursor, as defined earlier in this description, into contact optionally with at least one activator as defined earlier in this description and/or optionally with at least one additive as defined earlier in this description. Said contact is made advantageously in a solvent that is selected from among the aliphatic and cycloaliphatic hydrocarbons such as hexane, cyclohexane, heptane, butane or isobutane, aromatic hydrocarbons such as benzene, toluene, orthoxylene, mesitylene, ethylbenzene, and the chlorinated hydrocarbons such as chlorobenzene, pure or in a mixture. The aliphatic hydrocarbons such as n-heptane and the aromatic hydrocarbons such as orthoxylene are advantageously used. The concentration of the metal(s) selected from among titanium, zirconium, hafnium, nickel and iron in the catalytic solution is advantageously between $1.10^{-4}$ and 1 mol/L. The molar ratio between the activator and said metal precursor is advantageously between 1/1 and 1800/1, preferably between 2/1 and 800/1, and in an even more preferred manner between 3/1 and 100/1. The temperature at which the components of each of the catalytic systems are mixed is advantageously between −10 and 180° C., preferably between 0 and 150° C., for example at a temperature that is close to ambient temperature (15 to 30° C.). The mixture can be made under an atmosphere of ethylene or inert gas.

Said first oligomerization stage a) and said second oligomerization stage b) advantageously operate under a total pressure of 0 to 20 MPa, preferably 1 to 10 MPa, and at a temperature of 20 to 180° C., preferably 40 to 140° C.

The oligomerization stages of the process according to the invention are advantageously implemented continuously.

The implementation of the first oligomerization stage can preferably take place in a stirred reactor. The solution that contains the catalytic system is injected, into the oligomerization reactor that operates in liquid phase, simultaneously with the ethylene feedstock that is introduced by a valve that makes it possible to keep the pressure constant within the reactor. The reactor is an isothermal and stirred reactor. It is selected from among the stirred reactors that are known to one skilled in the art, in particular it may involve a reactor that is stirred mechanically and is cooled by a double jacket or an internal coil, or in a preferred manner stirred by external recirculation with a recycling having been advantageously cooled so as to extract the reaction heat. The recycling is inside the oligomerization unit; it is not shown in FIG. 1. A valve makes it possible to keep the liquid level constant, thus making it possible to extract from the reactor a mass flow rate that is equal to the mass flow rate of the fluids that are introduced (catalytic system, C2 ethylene feedstock and optional recycling). The first oligomerization stage can advantageously take place in one or more reactors in a series or in parallel. The implementation of the second oligomerization stage can advantageously take place in any type of reactor and in particular in a tubular or stirred reactor. In a preferred manner, it is produced in a tubular-type reactor where the heat is evacuated by means of a double jacket that covers the tube. The liquid feedstock is advantageously introduced with the activator and/or with at least one additive that is optionally present in the catalytic system.

In one particular embodiment of the catalytic reactions for intermittent oligomerization, the same type of reactor is advantageously used in said stages a) and b) as those used for continuous implementation. The solution that contains the catalytic system for the implementation of said first oligomerization stage is injected into the oligomerization reactor that operates in liquid phase, simultaneously with the ethylene feedstock that is introduced by a valve that makes it possible to keep the pressure within said reactor constant. The products that are formed accumulate in the reactor where said second oligomerization stage takes place. At the end of the reaction, the reactors are cooled, the catalytic systems are destroyed by injection of amine, for example, and the products that are obtained are extracted and then washed.

In a preferred variant embodiment of the process of the invention, a stage for draining ethylene is implemented between the first and second oligomerization stages a) and b). The hydrocarbon effluent that is obtained from the first stage a) is advantageously subjected to a stage for draining ethylene in such a way as to produce at least one effluent that comprises a residual quantity of ethylene that is advantageously less than 5% by weight and preferably less than 1% by weight relative to the total mass of olefins that are present in said effluent. This stage for draining the ethylene is advantageously implemented by any means that stops the introduction of ethylene and that thus makes possible the chemical consumption of the ethylene for the benefit of the formation of olefins with a higher boiling point. For example, for a process that operates intermittently, drainage is advantageously implemented by closing an ethylene supply valve at the input of the reactor that implements said first oligomerization stage. The pressure within the reactor that implements said first oligomerization stage decreases until becoming stable, which is a sign of the consumption of the residual ethylene in favor of the formation of olefins with a higher molecular weight. For a process that operates continuously, the effluent that is obtained from the first oligomerization stage a) is advantageously sent into a tubular reactor without an addition of make-up ethylene. The length of this tubular reactor is advantageously long enough to make possible the consumption of ethylene dissolved in the effluent obtained from the first oligomerization stage a) in favor of the formation of olefins with a higher boiling point. In a surprising way, this stage for draining the ethylene makes it possible to increase significantly the proportion by weight of the C10-C24 olefinic fraction in the mixture of olefins that is present in the hydrocarbon effluent that is obtained at the end of said second oligomerization stage b).

According to the invention, the liquid hydrocarbon effluent that exits from said second oligomerization stage b) comprises the homogeneous catalytic systems that are used in each of said stages a) and b), which are soluble in the oligomerization products.

According to a particular embodiment of the process according to the invention, the liquid hydrocarbon effluent that exits from said second oligomerization stage b) is subjected to a treatment of said catalytic systems, whereby said treatment comprises at least one stage for neutralization of said catalytic systems and preferably at least one stage for separation of said deactivated catalytic systems, subsequent to said neutralization stage, for obtaining an olefinic effluent that contains the deactivated homogeneous catalytic systems from which oligomerization products have been stripped. Said neutralization stage and said stage for separating homogeneous catalytic systems are implemented according to the means that are known to one skilled in the art. For example, the neutralization is advantageously carried out by adding a base or an acid, in particular by alcohols, fatty acids, fatty amines, and ammonia. For a zirconium-based catalytic system, the neutralization is advantageously carried out according to the teaching that appears in the patent applications WO 2007/016990 and US2009/0314986. The separation of the homogeneous catalytic systems is advantageously carried out by washing with an aqueous solution. When said homogeneous catalytic systems are soluble in the aqueous phase, they are advantageously separated from the organic phase by decanting.

In accordance with said stage c) of the process of the invention, said olefinic hydrocarbon effluent that is obtained from said second oligomerization stage b), from which said deactivated catalytic systems are preferably stripped, is subjected to at least one fractionation stage in such a way as to recover at least one olefin-enriched olefinic stream having a number of carbon atoms that is greater than or equal to 9. Said olefinic stream advantageously comprises olefins that have 9 to 16 carbon atoms per molecule and in a very preferred manner 10 to 14 carbon atoms per molecule. In a preferred manner, said stream comprises at least 90% by weight of olefins having a number of carbon atoms that is greater than or equal to 9, and in a very preferred manner, said stream consists entirely of olefins having a number of carbon atoms that is greater than or equal to 9. When the ethylene feedstock that is used in said stage a) of the process of the invention comes from the reaction for dehydration of bioethanol, the C9+ olefins, preferably the C9-C16 olefins, and very preferably the C10-C14 olefins, present in said stream, are called C9+ bio-olefins, preferably C9-C16 bio-olefins, and very preferably C10-C14 bio-olefins because they initially come from a feedstock that is obtained from a renewable carbon source.

The fractionation stage according to said stage c) of the process according to the invention advantageously produces at least one olefin-enriched olefinic stream having a number of carbon atoms that is greater than or equal to 9, more preferably having a number of carbon atoms of between 9 and 16, and even more preferably having a number of carbon atoms of between 10 and 14, for example a C9+ bio-olefin stream and more preferably a C9-C16 bio-olefin stream, and even more preferably a C10-C14 bio-olefin stream, at least one olefin-enriched olefinic stream having a number of carbon atoms of between 4 and 8, for example a C4-C8 bio-olefin stream, and at least one olefin-enriched olefinic stream having a number of carbon atoms that is greater than 14 and even greater than 16. At least one part of said olefin-enriched olefinic stream having a number of carbon atoms of between 4 and 8 is advantageously recycled to said second oligomerization stage b) of the process according to the invention and mixed with the feedstock of stage b).

Said fractionation stage c) according to the process of the invention is implemented by any method that is known to one skilled in the art, for example by distillation.

In accordance with the process according to the invention, said C9+-olefin-enriched stream, produced at the end of said fractionation stage c), is used as a feedstock for the implementation of said alkylation stage in accordance with said stage d) that is described below in this description. Said C9+-olefin-enriched stream comprises a mixture of linear and branched C9+ olefins. The branched olefins are in the majority relative to the linear olefin, i.e., said C9+-olefin-enriched olefinic stream comprises at least 50% by weight of branched olefins. Said branched olefins have a number of branches that is advantageously between 1 and 5. The number of branches is advantageously determined by NMR of carbon.

In accordance with stage d) of the process according to the invention, said C9+-olefin-enriched stream, produced at the end of said fractionation stage c), is introduced into at least one reactor that carries out the alkylation of said C9+ olefins, preferably C9-16 olefins, and very preferably C10-C14 olefins, by at least one aromatic feedstock that comprises at least one compound having a benzene core. Said C9+-olefin-enriched stream, used as a feedstock for the implementation of said alkylation stage d), comprises at least 90% by weight of olefins having a number of carbon atoms that is greater than or equal to 9, and in a very preferred manner, said stream consists entirely of olefins having a number of carbon atoms that is greater than or equal to 9. In an even more preferred manner, said stream consists entirely of C9-C16 olefins and very preferably of C10-C14 olefins.

According to said alkylation stage d), said aromatic feedstock can come from any source that is known to one skilled in the art. In a preferred manner, said aromatic feedstock comprises, preferably consists of, benzene. Said aromatic feedstock that is used for the implementation of said stage d) is, for example, obtained from a fossil source, in particular petroleum or carbon. In an advantageous manner, it is obtained from a renewable source: in particular, said aromatic feedstock is advantageously obtained by transformation of bioethanol on a zeolitic acid catalyst or by transformation of glucose for producing aromatic compounds, including benzene. The transformation of bioethanol into benzene on a zeolitic acid catalyst has already been described by Madeira et al. (Applied Catalysis. A, 2009, Vol. 367, Nos. 1=2, 39-46). The zeolite ZSM-5 is particularly preferred in the composition of the zeolitic catalyst. The transformation of glucose into benzene was described by Carlson et al. (Journal of Catalysis, 270, 2010, 100-124).

Said alkylation stage d) is implemented in at least one reactor that operates either by homogeneous catalysis or by heterogeneous catalysis. For an implementation of said stage d) by homogeneous catalysis, said reactor is provided with at least one liquid acid catalyst, preferably hydrofluoric acid HF or sulfuric acid $H_2SO_4$. For an implementation of said stage d) by heterogeneous catalysis, said reactor is provided with at least one solid acid catalyst, in particular an amorphous acid catalyst or a zeolitic acid catalyst. A preferred amorphous acid catalyst comprises at least one silica-alumina or a fluoridated silica-alumina, A preferred zeolitic acid catalyst comprises at least one zeolite that is selected from the group that consists of zeolites of the following structural types: FAU, MOR, MTW, OFF, MAZ, BEA and EUO. Among the FAU-structural-type zeolites, the Y zeolite and the Y zeolite exchanged with rare earths (REY) are preferred. Among the MOR-structural-type zeolites, the mordenite zeolite is preferred. Among the MTW-structural-type zeolites, the zeolite ZSM-12 is preferred. Among the OFF-structural-type zeolites, the offretite zeolite is preferred. Among the MAZ-structural-type zeolites, the zeolite ZSM-4 is preferred. Among the BEA-structural-type zeolites, the beta zeolite is preferred, and among the EUO-structural-type zeolites, the zeolite EU-1 is preferred. Said zeolitic acid catalyst advantageously comprises a mixture of zeolites of different structural types, for example a mixture of at least two zeolites of different structural types selected from among the zeolites of the following structural types: FAU, MOR, MTW, OFF, MAZ, BEA and EUO. It may involve in particular a mixture of zeolites that consists of at least one Y zeolite and at least one MOR-structural-type zeolite, preferably a mordenite. The zeolite(s) present in the alkylation catalyst preferably comprise(s) at least one element X that is selected from among silicon and germanium, very preferably silicon, and at least one element T that is selected from among aluminum, iron, gallium and boron, very preferably aluminum, according to an overall X/T atomic ratio that is greater than or equal to 4. The zeolite(s) present in the alkylation catalyst generally come(s) in acid form in such a way that the content of alkaline element, in particular sodium, is such that the alkaline element/T atomic ratio is less than 0.5, preferably less than 0.1, and in a more preferred manner less than 0.02.

In a very preferred manner, said stage g) is implemented in the presence of at least one zeolitic catalyst, preferably in the presence of at least one catalyst that comprises at least one Y zeolite and very preferably one dealuminified Y zeolite.

Said alkylation catalyst advantageously comprises at least one oxide matrix, in particular alumina or silica. It comes in the form of seeds of different shapes and sizes. It is preferably used in the form of cylindrical or multilobar extrudates, such as extrudates that are bilobar, trilobar, or polylobar of straight or twisted shape, but it can optionally be manufactured and used in the form of crushed powder, tablets, rings, balls, or disks. A preferred zeolitic catalyst contains 1 to 95% by weight, preferably 3 to 90% by weight, and more preferably 5 to 85% by weight of at least one zeolite that is selected from among the zeolites of the following structural types: FAU, MOR, MTW, OFF, MAZ, BEA and EUO, and at least one matrix that ensures the make-up to 100% by weight.

With implementation by heterogeneous catalysis, said alkylation stage d) advantageously operates at a temperature of between 30 and 400° C., preferably between 50 and 350° C., and in a very preferred manner between 70 and 300° C., at a pressure of between 0.1 and 10 MPa, preferably between 1 and 7 MPa, and with an hourly volumetric flow rate of between 0.01 and 200 $h^{-1}$, preferably between 0.5 and 80 $h^{-1}$ (volume of liquid hydrocarbons corresponding to the olefinic stream and to the aromatic feedstock per volume of catalyst and per hour). The aromatic feedstock/olefinic stream molar ratio is between 2 and 50, preferably between 5 and 35. Said stage d) preferably implements at least one alkylation catalyst that operates in a fixed bed or in a moving bed. A preferred embodiment of said alkylation stage g), when said catalyst is a solid acid catalyst, consists in implementing at least two alkylation reactors in parallel in such a way as to allow the rejuvenation of the alkylation catalyst that is present in the reactor that does not operate in operational mode. Such an implementation is described in particular in the patent application US 2009/062583.

With implementation by homogeneous catalysis, said alkylation stage d) advantageously operates at a temperature of between 10 and 80° C., preferably between 20 and 60° C., and in a preferred manner between 30 and 50° C. The operating pressure is such that the reagents and the acid catalyst are in the liquid phase; thus, the pressure is advantageously between 0.2 and 4 MPa, preferably between 0.2 and 3 MPa. The acid/hydrocarbon feedstock volumetric ratio is between 0.1 and 10, and preferably between 1 and 3. The (compound(s) having a benzene core that is present in the aromatic feedstock)/olefins molar ratio is generally between 1 and 15, and preferably between 5 and 12. The contact time in the reactor is between 5 and 50 minutes and preferably between 20 and 40 minutes.

Said alkylation stage d) leads to the production of a mixture of aromatic compounds belonging to the family of alkylbenzenes. More specifically, said mixture comprises at least one aromatic compound whose benzene core carries at least one saturated and linear alkyl chain, preferably a single saturated and linear alkyl chain (linear monoalkylbenzene), having at least 9 carbon atoms, preferably having between 9 and 16 carbon atoms, and in a more preferred manner having between 10 and 14 carbon atoms, and at least one aromatic compound whose benzene core carries at least one saturated and branched alkyl chain, preferably a single saturated and branched alkyl chain (branched monoalkylbenzene), having at least 9 carbon atoms, preferably having between 9 and 16 carbon atoms, and in a more preferred manner having between 10 and 14 carbon atoms. In an advantageous manner, the branched (mono)alkylbenzene(s) that is/are produced has/have a saturated alkyl chain that carries from 1 to 5 branches. In accordance with the invention, the mixture of aromatic compounds that are produced at the end of said alkylation stage d) at the same time comprises (a) compound(s) belonging to the known family of the LAB referring to the linear alkylbenzenes, more preferably to the family of linear monoalkylbenzenes, and (a) compound(s) belonging to the family of the MAB referring to the modified alkylbenzenes and more specifically to the family of modified monoalkylbenzenes. The monoalkylbenzenes that are produced by the process of the invention are for the most part modified monoalkylbenzenes, i.e., at least 50% by weight, preferably at least 60% by weight, of the monoalkylbenzenes that are produced are monoalkylbenzenes whose alkyl chain is branched, preferably by a methyl group.

According to a particular embodiment of the process according to the invention, the effluent that is obtained from said alkylation stage is fractionated in such a way as to collect separately at least one first fraction containing said compound that is present in the aromatic feedstock, preferably benzene, at least a second fraction that contains the mixture of aromatic compounds that belong to the family of alkylbenzenes, preferably containing at least one aromatic compound that belongs to the family of linear alkylbenzenes, and at least one aromatic compound that belongs to the family of modified monoalkylbenzenes, and at least a third fraction that contains at least one polyalkylbenzene, in particular at least one dialkylbenzene.

Figure 1:
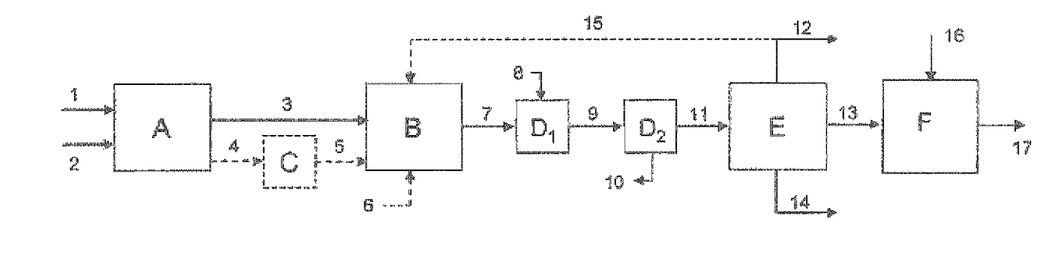
FIG. 1 diagrammatically shows the process for production of a mixture of aromatic compounds that belong to the family of alkylbenzenes starting from an ethylene feedstock, whereby said process comprises at least a first oligomerization stage followed by a second oligomerization stage, a stage for draining ethylene optionally being implemented between said oligomerization stages, which operate in the presence of a homogeneous catalytic system.

The ethylene feedstock is introduced into a first reaction zone (A), via the pipe (1), in which said feedstock is subjected to a first oligomerization stage. The homogeneous catalytic system that is used in the first reaction zone (A) is introduced via the pipe (2). The hydrocarbon effluent that is produced in the reaction zone (A) exits from this zone via the pipe (3) and is sent into a second reaction zone (B) in which it is subjected to a second oligomerization stage in the presence of a homogeneous catalytic system, identical or different from the one that is used in the reaction zone (A).

According to a variant of the process that consists in using two identical homogeneous catalytic systems in the reaction zones (A) and (B), i.e., the transition metal(s) present in said metal precursor(s) is (are) identical in each of said catalytic systems, an activator and/or an additive can be introduced into the reaction zone (B) via the pipe (6) that is shown in dotted lines. According to another variant of the process that consists in using different catalytic systems in the reaction zones (A) and (B), a homogeneous catalytic system that is different from the one that is used in the reaction zone (A), i.e., containing a metal precursor whose transition metal is different from the one that is present in the catalytic system that is used in the reaction zone (A), is introduced into the second oligomerization stage (B) via the pipe (6) that is shown in dotted lines. An activator and/or at least one additive can also be introduced into the second oligomerization stage (B) via the pipe (6) that is shown in dotted lines.

According to a preferred variant of the process of the invention, a zone (C) for draining ethylene that is shown in dotted lines is implemented between the two reaction zones (A) and (B), whereby said zone for draining ethylene comprises a pipe (4) for introducing the effluent that is obtained from the reaction zone (A) and a pipe (5) for the discharge of the effluent.

The reaction zone (B) is followed by a zone D for treatment of catalytic systems (zones D1 and D2): it comprises a pipe (8) for the introduction of chemical compounds allowing the neutralization of catalytic systems in the zone (D1), a pipe (9) for the introduction of the effluent that is obtained from the zone (D1) in the separation zone {oligomerization products/deactivated catalytic systems} (D2), and a pipe (10) allowing the extraction of deactivated catalytic systems.

The separation zone (D2) is followed by a zone (E) for separation of the oligomerization products that are obtained from the preceding stages: said zone (B) comprises a pipe (11) for the introduction of the effluent that is obtained from the separation zone (D2) and that comprises said oligomerization products, a pipe (12) for collecting an olefin-enriched olefinic fraction having a number of carbon atoms of between 4 and 9, whereby said C4-C9 fraction is optionally partially recycled via the pipe (15) toward the reaction zone (B), a pipe (13) for collecting an olefin-enriched olefinic fraction that has a number of carbon atoms of between 10 and 14, and a pipe (14) for collecting an olefin-enriched olefinic fraction that has a number of carbon atoms that is greater than 14. The C10-C14 olefinic fraction, collected by the pipe (13), is introduced into an alkylation zone (F) in the presence of an aromatic feedstock (16) that comprises benzene. The effluent (17) that is produced at the end of said alkylation zone comprises the mixture of desired modified and linear monoalkylbenzenes that are collected separately in a fraction that is obtained after the implementation of a fractionation stage, not shown in FIG. 1, of the effluent (17).

The following example illustrates the invention without limiting its scope.

EXAMPLE

This example implements the concatenation of the process according to the invention, namely a first stage for oligomerization of ethylene a) followed by a stage for draining ethylene, and then a second oligomerization stage b) in which the catalytic system that is used is identical to the one that is used in the first stage. An activator injection (TEA) is carried out in the second oligomerization stage b) that makes possible the increase in the yield of the C10+ olefinic fraction, as well as that of the selectivity toward the C10+ branched olefins to the detriment of the selectivity toward the linear olefins.

In a stainless steel autoclave with a useful volume of 250 ml, equipped with a double jacket that makes it possible to regulate the temperature by circulation of water or oil, the following are introduced in order under an argon atmosphere and at ambient temperature: 20 ml of cyclohexane, 3.5 ml of an orthoxylene solution that contains 0.2 mmol of $ZrCl_4$, and 0.2 mmol of di(2-ethylhexyloxy)-2,2-propane. Next, 1.2 mmol of ethyl aluminum sesquichloride $Al_2Et_3Cl_3$ (EASC), previously solubilized in 2.5 ml of orthoxylene, or a molar ratio of Al/Zr=12, is introduced. The temperature is then brought to 100° C. while introducing ethylene into the autoclave in such a way as to maintain a constant pressure of 3.5 MPa. The reaction is allowed to continue for one hour.

After 1 hour of reaction, introduction of ethylene is stopped. At the end of the draining of ethylene, the residual quantity of ethylene in the effluent is less than 0.5% by weight relative to the total mass of olefins present in said effluent. 3 ml of a xylene solution that contains 0.8 mmol of triethylaluminum (TEA) is injected. Stirring is maintained. The pressure is maintained at 3.5 MPa. The temperature is maintained at 100° C. for 4 additional hours. The stirring is then stopped, and the reactor cools to 20° C. Next, approximately 1 ml of dodecylamine is injected into the autoclave in such a way as to neutralize the entire catalytic system. The autoclave is then depressurized, and a gaseous fraction and a liquid fraction that are analyzed by chromatography are collected.

The liquid olefinic effluent is subjected to a fractionation stage, by distillation, in such a way as to collect an olefinic effluent that comprises olefins that have 4 to 9 carbon atoms, an olefinic effluent that comprises olefins that have 10 to 14 carbon atoms, and an olefinic effluent that comprises olefins that have at least 15 carbon atoms.

The distribution of olefins, determined by gas phase chromatography (GPC), as well as the measurement of linearity, per fraction, of the olefins obtained are provided in Table 1.

TABLE 1

Distribution and Linearity of the Olefins that are Obtained

| | Distribution (% by Weight of Olefins Per Number of Carbon Atoms) | Linearity Per Carbon Number (% by Weight) |
|---|---|---|
| C4-C9 | 28.9 | 76 |
| C10-C14 | 30.4 | 34.5 |
| C15+ | 40.7 | <15 |

The mean linearity, expressed in terms of percentage, is the ratio of the percentage of linear olefins present in the analyzed fraction (respectively the C4-C9 fraction, the C10-C14 fraction, and the C15+ fraction) to the total percentage of olefins present in said fraction. The olefins that are present in the C10-C14 olefinic fraction have a linearity that is equal to 34.5% and are therefore branched for the most part. Said C10-C14 olefinic fraction is used as a feedstock for the alkylation reaction.

The reaction for alkylation of benzene in the presence of said C10-C14 olefinic feedstock that is obtained above is carried out in a catalytic reactor that comprises only a single reaction zone that contains 50 cm³ of a zeolitic catalyst in the form of extrudates. The alkylation catalyst contains a commercial USY zeolite, having a content by weight of sodium of 0.14% and an Si/Al atomic ratio that is equal to 38, The zeolite is shaped by extrusion with alumina in such a way that the alkylation catalyst is formed by 50% by weight of USY zeolite and 50% by weight of alumina. Next, the extrudates are dried and then calcined at 550° C.

The operating conditions for the alkylation of benzene by the C10-C14 olefins are the following:

Temperature: 135° C.
Pressure: 4 MPa
VVH (hourly volumetric flow rate)=1 h$^{-1}$ (cm³ of benzene feedstock+C10-C14 olefins per cm³ of catalyst and per hour)
Benzene/C10-C14 olefins molar ratio: 30

A feedstock that contains a mixture that is formed by benzene and C10-C14 olefins is prepared. This feedstock is introduced at the input of the catalytic reactor where the alkylation reaction takes place.

The results that are obtained are presented in Table 2. They are expressed in terms of stability of the catalyst and the selectivity toward the modified alkylbenzenes.

TABLE 2

Results at the End of the Implementation of the Alkylation Stage

| Cycle Time with Conversion of C10-C14 Olefins >95% | >500 h |
|---|---|
| MAB Selectivity | 78% |

The MAB selectivity is defined as being equal to the mass ratio [MAB/(MAB LAB)], whereby the LAB are the linear alkylbenzenes and the MAB are the modified alkylbenzenes. The results that appear in Table 2 demonstrate the stability of the alkylation catalyst over a long period. The process according to the invention leads to the majority production of modified monoalkylbenzenes.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application Ser. No. 10/01949, filed May 6, 2010, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for the production of a mixture of aromatic compounds belonging to the family of alkylbenzenes in the presence of at least one aromatic feedstock that comprises at least one compound that has a benzene core and at least one olefinic stream that is produced from an ethylene feedstock, whereby said process comprises at least:
 a) a first oligomerization of said ethylene feedstock that consists of at least one hydrocarbon effluent that comprises a mixture of olefins having a number of carbon atoms that is for the most part between 4 and 30, whereby said mixture of olefins comprises a C10-C24 olefinic fraction that has a mean linearity that is greater than 60%, in the presence of at least one homogeneous catalytic system that contains at least one zirconium-based metal precursor and at least one compound of aluminum as an activator wherein said compound of aluminum is selected from a group comprising tris(hydrocarbyl)aluminums, hydrocarbylaluminum halides, and aluminoxanes,
 b) a second oligomerization of the effluent that is obtained from a) that consists of at least one hydrocarbon effluent that comprises a mixture of olefins having a number of carbon atoms that is for the most part between 4 and 30, whereby said mixture of olefins comprises a C10-C24 olefinic fraction that has a mean linearity that is less than 50%, in the presence of at least one homogeneous catalytic system that is identical to or different from the one that is used in said stage a), c) at least one fractionation of the effluent that is obtained from said oligomerization b) in such a way as to recover at least one olefin-enriched olefinic stream having a number of carbon atoms that is greater than or equal to 9 and wherein the olefin-enriched olefinic stream is comprised of at least 50% by weight of branched olefins, d) a alkylation of said olefinic stream that is obtained from c) by at least one aromatic feedstock that comprises at least one compound that has a benzene core.

2. The production process according to claim 1, such that said ethylene feedstock comes from a steam-cracking unit, an FCC unit, or a Fischer-Tropsch synthesis unit.

3. The production process according to claim 1, such that said ethylene feedstock comes from the reaction for dehydration of bioethanol, which is produced from a renewable source obtained from biomass.

4. The production process according to claim 1, such that the homogeneous catalytic system that is used in said first oligomerization stage a) contains at least one additive that is a a Bronsted acid compound, a Lewis acid or base, or an electron donor organic compound that contains at least one oxygen atom or at least one nitrogen atom or at least one phosphorus atom or at least one mono- or polyfunctional sulfur atom.

5. The production process according to claim 1, such that in said homogeneous catalytic system, used for the implementation of said first oligomerization the at least one activator is based on ethyl aluminum sesquichloride.

6. The production process according to claim 1, such that the homogeneous catalytic system that is used in said second oligomerization b) is identical to the one that is used in said first oligomerization stage a).

7. The production process according to claim 6, such that the homogeneous catalytic system that is used in said second oligomerization b) contains a metal precursor based on zirconium, a first activator based on ethyl aluminum sesquichloride, and at least one second activator based on triethylaluminum (TEA).

8. The production process according to claim 1, such that said first oligomerization a) and said second oligomerization b) operate under a total pressure of 0 to 20 MPa, and at a temperature of 20 to 180° C.

9. The production process according to claim 1, such that the liquid hydrocarbon effluent that exits from said second oligomerization b) is subjected to a treatment of said catalytic systems, whereby said treatment comprises at least one neutralization of said catalytic systems and at least one stage for separation of said deactivated catalytic systems, subsequent to said neutralization.

10. The production process according to claim 1, such that said olefinic stream that is obtained from c) comprises olefins having 10 to 14 carbon atoms per molecule.

11. The production process according to claim 1, such that said olefin-enriched olefinic stream having a number of carbon atoms that is greater than or equal to 9 comprises a mixture of linear and branched C9+ olefins.

12. The production process according to claim 11, such that said branched olefins have a number of branches of between 1 and 5.

13. The production process according to claim 1, such that said alkylation d) is implemented in at least one reactor that operates either by homogeneous catalysis or by heterogeneous catalysis.

14. The process according to claim 1, such that said mixture comprises at least one aromatic compound whose benzene core carries at least one saturated and linear alkyl chain having at least 9 carbon atoms and at least one aromatic compound whose benzene core carries at least one saturated and branched alkyl chain having at least 9 carbon atoms.

* * * * *